United States Patent
McIntyre et al.

(10) Patent No.: US 9,561,021 B2
(45) Date of Patent: Feb. 7, 2017

(54) METHOD AND SYSTEM FOR INTRACAVITARY AND EXTRACAVITARY PROCEDURES

(75) Inventors: Jon T. McIntyre, Newton, MA (US); Barry Weitzner, Acton, MA (US); Paul DiCarlo, Middleboro, MA (US); Paul Smith, Smithfield, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 969 days.

(21) Appl. No.: 13/094,736

(22) Filed: Apr. 26, 2011

(65) Prior Publication Data

US 2011/0276038 A1    Nov. 10, 2011

Related U.S. Application Data

(60) Provisional application No. 61/332,028, filed on May 6, 2010.

(51) Int. Cl.
*A61B 17/00* (2006.01)
*A61B 17/42* (2006.01)
(Continued)

(52) U.S. Cl.
CPC ......... *A61B 17/00234* (2013.01); *A61B 17/42* (2013.01); *A61B 17/29* (2013.01);
(Continued)

(58) Field of Classification Search
CPC ..................................................... A61B 17/00
(Continued)

(56) References Cited

U.S. PATENT DOCUMENTS

| 6,412,493 B1 | 7/2002 | Hsue |
| 2003/0216759 A1 | 11/2003 | Burbank et al. |

(Continued)

FOREIGN PATENT DOCUMENTS

| WO | WO 98/35616 A1 | 8/1998 |
| WO | WO 2004/105624 A1 | 12/2004 |

(Continued)

OTHER PUBLICATIONS

Dodgson, N.A., et al., "Autostereoscopic 3D Display in Laparoscopic Surgery," CAR 95 (Computer Assisted Radiology), Jun. 1995, pp. 1139-1144.
(Continued)

*Primary Examiner* — Lynsey Crandall
(74) *Attorney, Agent, or Firm* — Bookoff McAndrews, PLLC

(57) ABSTRACT

Embodiments include a method of performing a medical procedure in a patient. The method includes inserting a first working instrument and a second working instrument through an opening in the patient, creating an incision in body tissue inside the patient using at least one of the first and second working instruments, and advancing the second working instrument through the incision to position the second working instrument at a work site inside the patient. The method also includes positioning the first working instrument at the work site without advancing the first working instrument through the incision and performing a procedure at the work site inside the patient using the first and second working instruments.

20 Claims, 11 Drawing Sheets

(51) Int. Cl.
 *A61B 17/29* (2006.01)
 *A61B 17/32* (2006.01)
 *A61B 18/14* (2006.01)

(52) U.S. Cl.
 CPC ... *A61B 17/320016* (2013.01); *A61B 18/1492* (2013.01); *A61B 2017/003* (2013.01); *A61B 2017/00278* (2013.01); *A61B 2017/00477* (2013.01); *A61B 2017/00876* (2013.01); *A61B 2018/143* (2013.01); *A61B 2018/1432* (2013.01)

(58) Field of Classification Search
 USPC .............................................. 606/1; 128/898
 See application file for complete search history.

(56) References Cited

U.S. PATENT DOCUMENTS

| | | | |
|---|---|---|---|
| 2004/0176751 A1* | 9/2004 | Weitzner | A61B 17/0469 606/1 |
| 2004/0242999 A1* | 12/2004 | Vitek et al. | 600/437 |
| 2005/0216041 A1 | 9/2005 | Okada et al. | |
| 2006/0100615 A1 | 5/2006 | McIntyre et al. | |
| 2007/0225745 A1 | 9/2007 | Arnal et al. | |
| 2008/0188890 A1 | 8/2008 | Weitzner et al. | |
| 2009/0118729 A1* | 5/2009 | Auth et al. | 606/42 |
| 2009/0149714 A1* | 6/2009 | Bonadio | A61B 1/32 600/201 |
| 2009/0306471 A1* | 12/2009 | Gettman | 600/104 |

FOREIGN PATENT DOCUMENTS

| | | |
|---|---|---|
| WO | WO 2008/007355 A1 | 1/2008 |
| WO | WO 2008/083318 A2 | 7/2008 |
| WO | WO 2009/038725 A1 | 3/2009 |

OTHER PUBLICATIONS

Viking Systems, "Operate with a True View in 3D: EndoSite 3Di Digital Vision System," 2004, 6 pages.

Visionsense, "VSII-Visionsense Stereoscopic Vision System: A Miniature Microscope in Endoscopic Proportions," available at http://www.visionsense.com/html/product/product.htm, printed on Sep. 23, 2009, 2 pages.

International Search Report and Written Opinion issued in PCT International Application No. PCT/US2011/035108 mailed Aug. 17, 2011 (15 pages).

* cited by examiner

US 9,561,021 B2

METHOD AND SYSTEM FOR INTRACAVITARY AND EXTRACAVITARY PROCEDURES

This application claims the benefit of priority from U.S. Provisional Application No. 61/332,028, filed May 6, 2010, which is herein incorporated by reference in its entirety.

FIELD

Embodiments of the present invention generally relate to medical devices. Specifically, embodiments of the present invention relate to a device for use in medical applications, such as for intracavitary and extracavitary procedures. Embodiments of the present invention also cover methods of using such devices. Those skilled in the art will recognize the benefits of applying the present invention to similar fields not discussed herein.

BACKGROUND

In general, it is desirable to minimize the invasiveness of medical procedures. These medical procedures may include therapeutic or diagnostic medical procedures. Invasive medical procedures are generally more expensive, and there is generally a greater risk of complication and discomfort for the patient. For example, open surgery, for a therapeutic or diagnostic purpose, is an invasive medical procedure with significant attendant risks. Since the performance of open surgery typically requires relatively large incisions, relatively large amounts of blood may be lost, the risk of infection may increase, and the potential for post-operative hernias may be higher. Furthermore, relatively large incisions require extended recovery times to allow the incisions to heal. For example, the treatment of uterine fibroids, such as by open myomectomy or hysterectomy, can involve an abdominal incision and/or complete removal of the uterus, and therefore can be very invasive. Accordingly, methods and devices that reduce trauma to the patient, are less invasive, and/or enhance access to the patient would be beneficial.

It is to be understood that both the foregoing general description and the following detailed description are exemplary and explanatory only and are not restrictive of the invention.

SUMMARY

In one aspect, a method of performing a medical procedure in a patient includes inserting a first working instrument and a second working instrument through an opening in the patient, creating an incision in body tissue inside the patient using at least one of the first and second working instruments, and advancing the second working instrument through the incision to position the second working instrument at a work site inside the patient. The method also includes positioning the first working instrument at the work site without advancing the first working instrument through the incision, and performing a procedure at the work site inside the patient using the first and second working instruments.

In another aspect, a method of performing a medical procedure in a patient includes inserting a first working instrument and a second working instrument through an opening in the patient, creating an incision in body tissue inside the patient using at least one of the first and second working instruments, and advancing the second working instrument through the incision to position the second working instrument at a work site inside the patient. The method also includes positioning the first and second working instruments near opposite sides of a wall of body tissue at the work site, and performing a procedure at the work site inside the patient using the first and second working instruments.

In a further aspect, a method of performing a medical procedure in a patient includes inserting a first working instrument and a second working instrument through an opening in the patient, creating a first incision in body tissue at a first location inside the patient using at least one of the first and second working instruments, and creating a second incision in body tissue at a second location inside the patient using at least one of the first and second working instruments. The first and second locations are different locations. The method also includes advancing the first working instrument through the first incision, advancing the second working instrument through the second incision, and performing a procedure at a work site inside the patient using the first and second working instruments after advancing the first and second working instruments through the respective first and second incisions.

In yet another aspect, a method of performing a medical procedure in or near a uterus of a patient includes advancing a first working instrument and a second working instrument through a vagina of the patient, creating an incision in a vaginal wall in the patient using at least one of the first and second working instruments, and advancing the second working instrument through the incision to position the second working instrument at a work site on or near the uterus. The method also includes positioning the first working instrument at the work site without advancing the first working instrument through the incision, and performing a procedure at the work site using the first and second working instruments.

In yet a further aspect, a device for performing a medical procedure in a patient includes a first working instrument including a distal end, and a second working instrument including a distal end. The first and second working instruments are configured to move independently from each other. The device also includes a connecting mechanism at the first and second distal ends of the first and second working instruments, and the connecting mechanism is configured to secure the distal end of the first working instrument to the distal end of the second working instrument when the distal ends of the first and second working instruments are disposed inside the patient.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The terms "proximal" and "distal" are used herein to refer to the relative positions of the components of the exemplary endoscopic device 10. When used herein, "proximal" refers to a position relatively closer to the exterior of the body or closer to the surgeon using the endoscopic device 10. In contrast, "distal" refers to a position relatively further away from the surgeon using the endoscopic device 10 or closer to the interior of the body.

Figure 1:
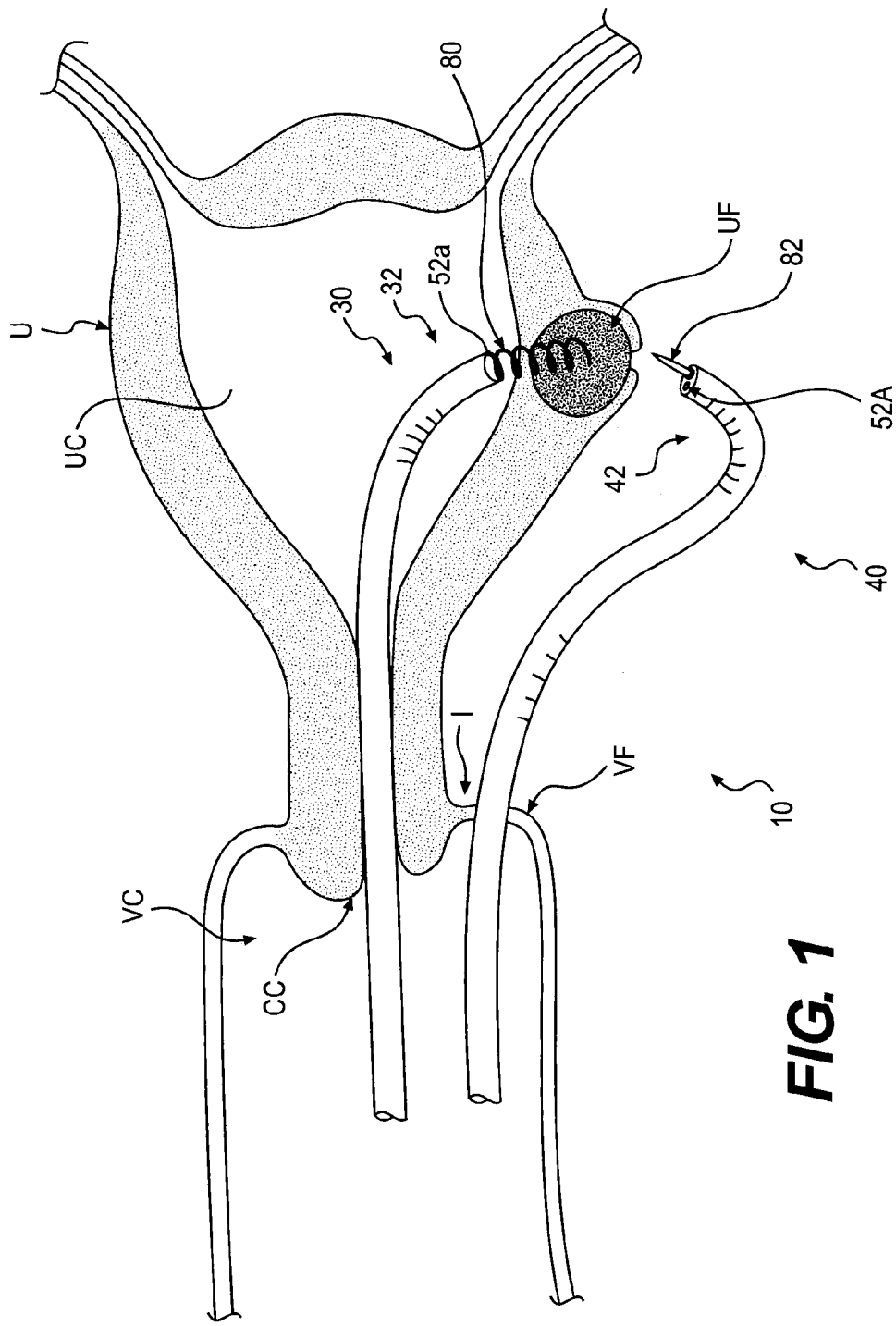
FIG. 1 is a cross-sectional view of a body portion showing a device for performing a myomectomy, the device including one working instrument extending into the uterine cavity and another working instrument extending outside the uterine cavity, according to an exemplary embodiment of the invention.

FIG. 1 depicts an exemplary endoscopic device 10 that may be used for any therapeutic or diagnostic endoscopic procedure. The phrase "endoscopic procedure" is broadly used to indicate any medical procedure that may be performed by inserting an endoscope, guide tube, catheter, or any other medical device into the body through any anatomic opening. Although in the description that follows, the endoscopic device 10 is described and shown as being inserted into the body through the vagina, it should be emphasized that this description is exemplary only. For example, the endoscopic device 10 may also be used for procedures in or near other body organs, such as uterus, pelvic area, bladder, stomach, esophagus, intestine or other organs in the lower gastrointestinal tract, heart, etc. For purposes of this disclosure, the phrase "body organ" is broadly used to include body lumens and body cavities.

In general, embodiments of the current disclosure may be applicable to applications where a medical device is inserted into the body through an anatomic opening (e.g., an incision or a natural orifice). For example, embodiments of the current disclosure may be used in, but are not limited to, natural orifice transluminal endoscopic surgery (NOTES) procedures or single incision laparoscopic surgical (SILS) procedures.

According to an embodiment, the endoscopic device 10 may include a guide sheath 20, a first probe or working instrument 30, and a second probe or working instrument 40. As described below, the endoscopic device 10 may be inserted into a patient to perform a surgical operation in the patient and/or to observe inside the patient. The endoscopic device 10 may be made of any suitable material capable of being inserted into the body, e.g., a suitable biocompatible material.

The guide sheath 20 may be inserted into the opening in the patient and advanced into the patient (e.g., advanced into a body organ, such as the vagina, and positioned as shown in FIGS. 2 and 5-9), and then the first and second working instruments 30, 40 may be advanced through the guide sheath 20 into the patient. As another alternative, the guide sheath 20 may be omitted or substituted by another suitable device known in the art.

The guide sheath 20, the first working instrument 30, and the second working instrument 40 may be configured to be at least partially inserted into an opening in the patient, such as a natural orifice in the body (e.g., mouth, rectum, anus, nose, urethra, umbilicus, vagina, etc.) or an incision created by the surgeon. The guide sheath 20, the first working instrument 30, and the second working instrument 40 may be advanced through the opening in the patient so that distal ends 32, 42 of the first and second working instruments 30, 40 may be positioned at or near a work site in the patient.

The guide sheath 20 may include one or more lumens 22, and one or more working instruments may be received in each lumen 22. The lumens 22 may extend longitudinally (axially) between a distal end and a proximal end of the guide sheath 20. As shown in FIGS. 2 and 5-9, the guide sheath 20 may include two lumens 22 with the first and second working instruments 30, 40 slidably received in the respective lumens 22. Alternatively, the guide sheath 20 may include one lumen 22 (e.g., with both working instruments 30, 40 slidably received in the lumen 22) or more than two lumens 22. For example, in addition to the lumens 22 through which the first and second working instruments 30, 40 are inserted, one or more of an aspiration lumen, an irrigation lumen, an illumination lumen, a viewing lumen, and a working lumen (e.g., for slidably receiving one or more additional working instruments) may run longitudinally through the guide sheath 20. The guide sheath 20 and the working instruments 30, 40 may be bent or articulated into a desired configuration to perform a procedure. Alternatively, the guide sheath 20 may be rigid. Some exemplary configurations of guide sheaths (or guide tubes) and working instruments are disclosed, for example, in U.S. patent application Ser. No. 11/946,790, entitled "Multi-Part Instrument Systems and Methods," which is hereby incorporated by reference in its entirety.

The surgeon may move each working instrument 30, 40 longitudinally (e.g., in the distal and proximal directions, axially), laterally (e.g., side to side), and/or rotationally with respect to the guide sheath 20 or any other portion of the endoscopic device 10. The working instruments 30, 40 may be flexible, rigid, bent, straight, malleable, etc. Each of the working instruments 30, 40 may be articulated to move at least a portion of the respective working instrument 30, 40 longitudinally, laterally, and/or rotationally with respect to another portion of the respective working instrument 30, 40.

Each working instrument 30, 40 may include an end effector 50 (see, e.g., FIG. 10) at the respective distal end 32, 42 of the working instrument 30, 40. The end effector 50 may include a device configured to assist in performing a surgical procedure. For example, the end effector 50 may include, but is not limited to, a cutting device (e.g., scissors, tissue cutter, etc.), forceps, a fixation device, a manipulation device, a dissection device, a support device, a sealing device, a needle holder, a closure device (e.g., clips, staples, loops, ligator, suturing device, etc.), a retrieval device (e.g., snare, basket, loop, a fluid extraction device, etc.), a tissue exploration device (e.g., optical device, illumination device, etc.), a tissue sampling device, a delivery device, a device for aiding in the patency of a lumen or for dilating an opening (e.g., a balloon or other expandable member, patency brush, stent, fan retractor, wire structure, etc.), a grasping device, a stabilizing device, an ablation device, a resection device, a pressure application device, an energy delivery device, etc. Examples of such devices will be described in detail below in connection with FIGS. 1-11. Each working instrument 30, 40 may include control wires or other devices connected to the end effector 50 to allow the surgeon to control the movement of the end effector 50. The end effector 50 may be connected to an articulating portion that allows the end effector 50 to move longitudinally, laterally, and/or rotationally with respect to another portion of the respective working instrument 30, 40. Accordingly, the working instruments 30, 40 and end effectors 50 may be any type of suitable working instruments and end effectors known to those skilled in the art.

One or more of the working instruments 30, 40 may include one or more lumens through which an additional working instrument including a "pop-up" end effector, such as one of the end effectors 50 described above, may be inserted as will be described in detail below. The additional working instrument may be moveable longitudinally, laterally, and/or rotationally to control the position of the additional working instrument with respect to the working instrument 30, 40 and the patient.

Alternatively, one or more of the working instruments 30, 40 may not include an end effector. For example, the working instrument 30, 40 may include a blunt and/or rounded tip for exploration and/or for assisting another working instrument or end effector (e.g., an obturator). As another alternative, the working instruments 30, 40 may include an open distal end for the delivery of a treatment fluid or solid and/or for collection of a body fluid or tissue sample, e.g., for irrigation and/or aspiration.

An optical device 52a, 52b may be embedded into or attached to one or more of the working instruments 30, 40 at or near the respective distal ends 32, 42 of the working instruments 30, 40, e.g., on the distal face or a circumferential or other outer surface near the distal ends 32, 42. The optical device 52a, 52b may include a camera, imaging sensor (e.g., a CMOS (complimentary metal-oxide semiconductor) imaging sensor), or other image receiving device (e.g., a fiber optic imaging device), which may transmit (e.g., wirelessly or using a wire, a fiber optic cable, or another type of cable embedded along the length of the working instrument 30, 40) an image signal to a monitor or other display device viewable by the surgeon.

Figure 10:
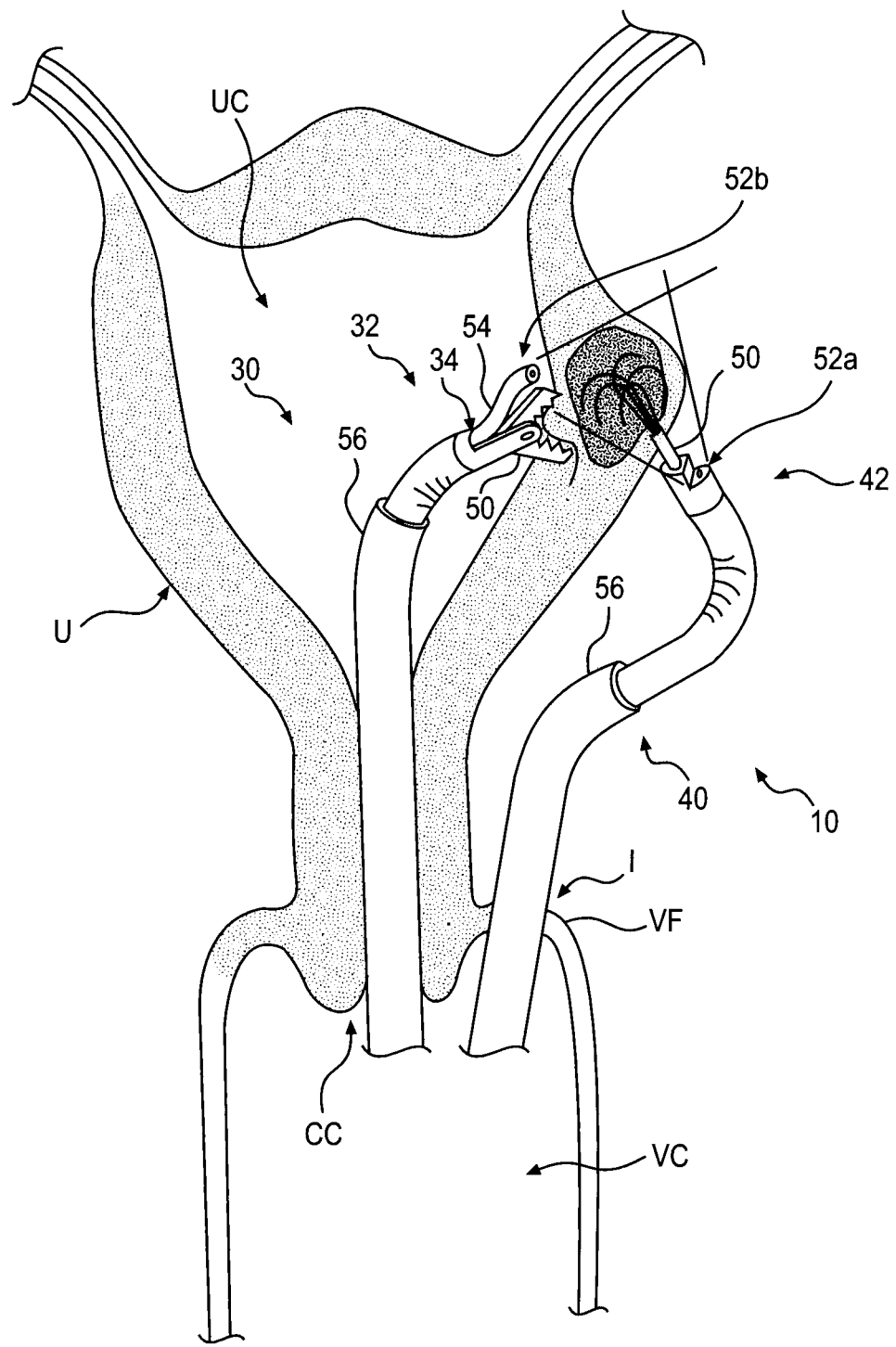
FIG. 10 is a cross-sectional view of a body portion showing a device inserted into a patient, the device including one working instrument with a pop-up optical device and another working instrument with an integral optical device, according to an exemplary embodiment of the invention.

FIG. 10 depicts two exemplary embodiments of optical devices 52a, 52b that may be included in one or both of the working instruments 30, 40. FIG. 10 and the corresponding description provided below relates to an embodiment in which the first working instrument 30 includes optical device 52b and the second working instrument includes optical device 52a. However, it is to be understood that either one of the optical devices 52a, 52b may be included on one or both of the first and second working instruments 30, 40.

An "integral" optical device 52a may be embedded or integral to the working instrument 40. With this type of optical device 52a, the surgeon may move the working instrument 40 longitudinally, laterally, and/or rotationally to control the position of the optical device 52a with respect to the patient.

A "pop-up" optical device 52b may be independently moveable with respect to the working instrument 30. For example, the optical device 52b may be embedded in or integral to a separate working instrument 54 slidably received in a lumen in the working instrument 30. The working instrument 54 may be coaxial with the working instrument 30 or may have an axis that is parallel to the axis of the working instrument 30. The surgeon may move the working instrument 30 and/or the working instrument 54 that includes the optical device 52b longitudinally, laterally, and/or rotationally to control the position of the optical device 52b with respect to the patient. The pop-up optical device 52b may also be positioned with respect to the working instrument 30 that slidably receives the working instrument 54 so that the pop-up optical device 52b provides a "bird's eye view" of the work site and other end effectors 50 included on the working instruments 30, 40.

Figure 11:
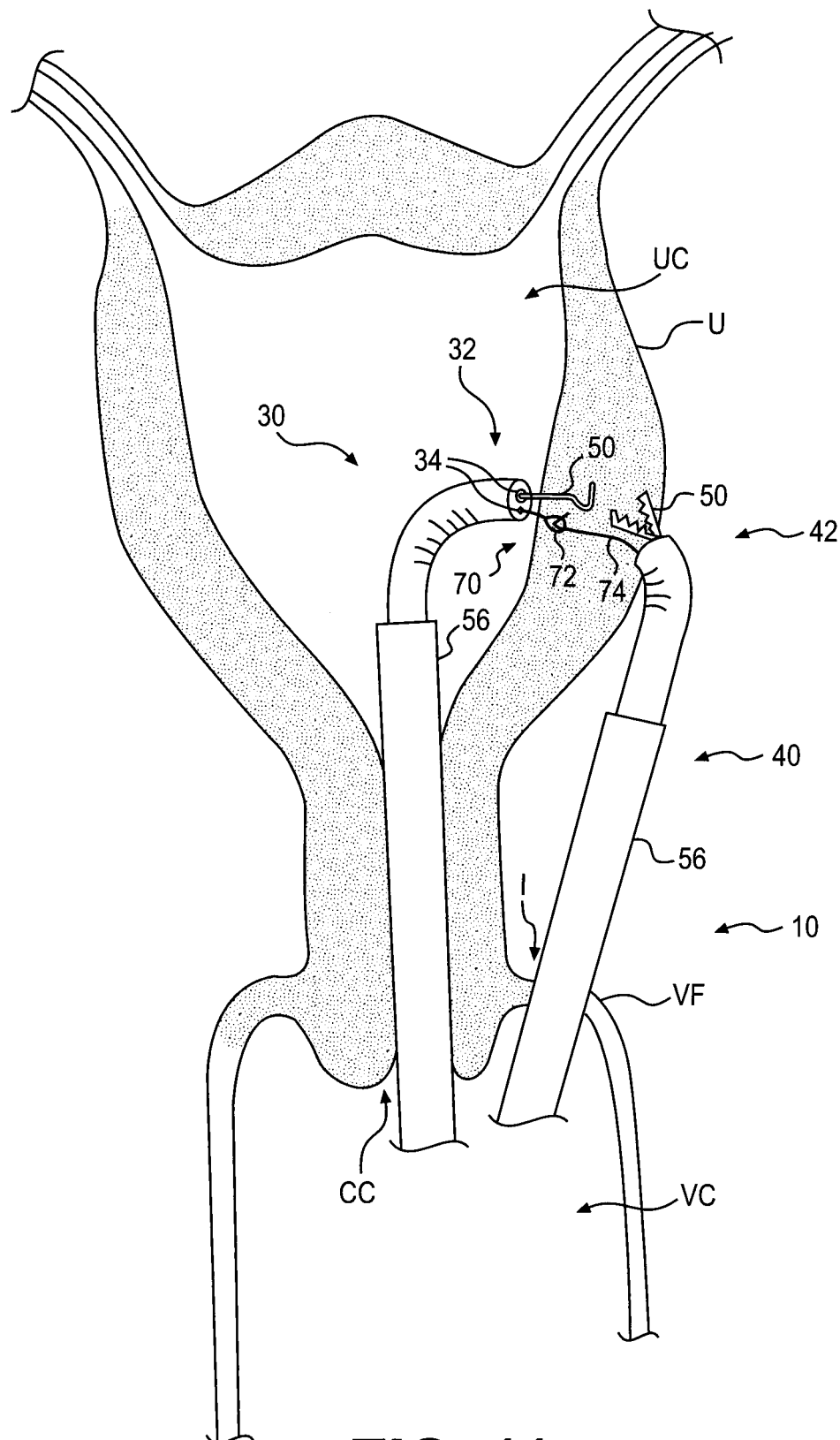
FIG. 11 is a cross-sectional view of a body portion showing a device inserted into a patient, the device including a connecting mechanism for connecting the distal ends of two working instruments together, according to an exemplary embodiment of the invention.

As shown in FIGS. 10 and 11, the working instruments 30, 40 may be slidably received in individual sheaths 56. Alternatively, these sheaths 56 may be omitted.

One or more of the working instruments 30, 40 may include a positioning device 60 (FIG. 5), such as a collar, to assist in positioning the working instrument 30, 40 and/or the end effector 50 of the working instrument 30, 40 in the patient, as will be described in detail below.

As shown in FIG. 11, the working instruments 30, 40 may communicate or interact with each other, e.g., by connecting together, etc. For example, the working instruments 30, 40 may communicate with each other by transillumination or with sound. As another example, the working instruments 30, 40 may include a connecting mechanism 70 that connects the two working instruments 30, 40 at the work site, e.g., to stabilize one of the working instruments 30, 40 with respect to the other.

FIG. 11 depicts the connecting mechanism 70 including a first element 72 slidably received in a lumen 34 in the first working instrument 30 and a second element 74 slidably received in a lumen in the second working instrument 40. The first and second elements 72, 74 are configured to connect to each other and may be positioned at the distal ends 32, 42 of the first and second working instruments 30, 40 so that the distal ends 32, 42 are connected together, e.g., when the distal ends 32, 42 are positioned at the work site. As shown in FIG. 11, the first element 72 may include a loop, and the second element 74 may include a hook, wire, or needle for inserting through the loop or otherwise engaging the first element 72. Alternatively, the first element 72 may include the hook, and the second element 74 may include the loop. As another alternative, one of the first or second elements 72, 74 may include a magnet, and the other of the first or second elements 72, 74 may include a ferrous material that is attracted to the magnet. It is to be understood that the first and second elements 72, 74 may include any combination of elements that are connectable or that may attract or engage each other.

The surgeon may connect, engage, or bring together the first and second elements 72, 74 before or while performing the procedure at the work site. While the distal ends 32, 42 of the working instruments 30, 40 are held together, the surgeon may use other end effectors 50 provided on the working instruments 30, 40 (e.g., embedded on the working instruments 30, 40 and/or slidably received in one or more lumens in the working instruments 30, 40) to perform a procedure at the work site. As a result, the surgeon does not have to actively hold the distal ends 32, 42 of the working instruments 30, 40 near each other. Also, the connecting mechanism 70 is capable of holding the distal ends 32, 42 of the working instruments 30, 40 facing each other while the working instruments 30, 40 are positioned at opposite sides of a wall of body tissue at the work site. As a result, the connecting mechanism 70 is effective when the surgeon wants to place the working instruments 30, 40 in this configuration. Furthermore, while the distal ends 32, 42 of the working instruments 30, 40 are held together, one of the working instruments 30, 40 may act as a backstop as the other working instrument 30, 40 cuts, ablates, or performs some other procedure.

FIGS. 1-11 depict various types of procedures that may be performed using the endoscopic device 10 at a work site in or near a uterus, vagina, and/or pelvic area of a patient, such as for the treatment of uterine fibroids, the treatment of endometriosis, the treatment of adhesions in the pelvic area, female sterilization, the treatment of diseases of the adnexal mass (e.g., in ovaries, fallopian tubes, uterine ligaments, etc.), and other procedures.

Treatment of uterine fibroids depends on the type of symptoms, the severity of the symptoms, the number of the fibroids, the location of the fibroids, etc. Myomectomy and hysterectomy are two types of treatment of uterine fibroids. A myomectomy results in the surgical removal of the uterine fibroids from the uterus and may involve an abdominal incision.

Figure 6:
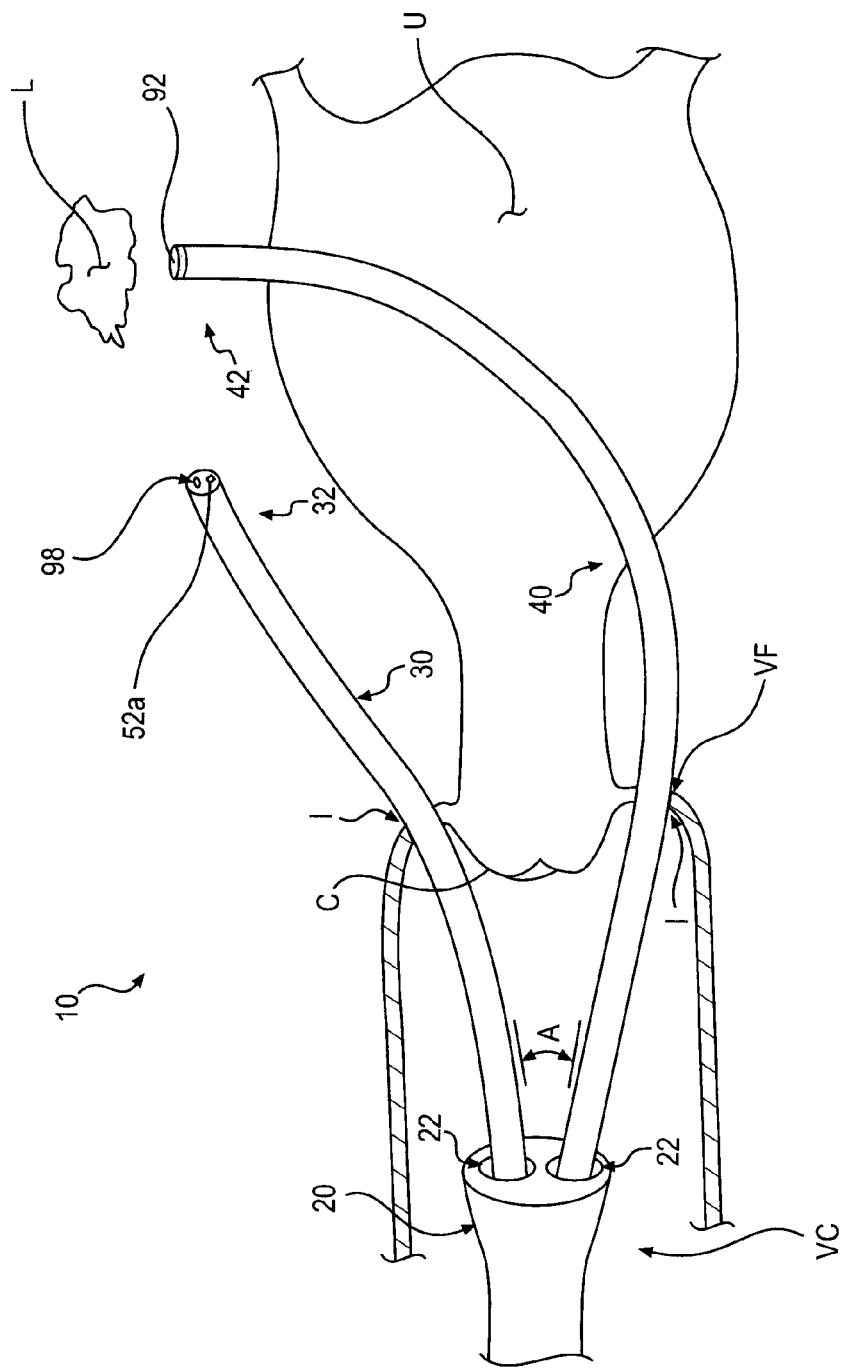
FIG. 6 is a cross-sectional view of a body portion showing a device for treating endometriosis, the device including two working instruments extending outside the uterine cavity, according to an exemplary embodiment of the invention.

FIG. 1 shows the endoscopic device 10 including the first and second working instruments 30, 40 for performing a myomectomy. The procedure described below may be advantageous for subserosal fibroids (located on the outside of the uterus). End effector(s) of the first working instrument 30, 30 may include a stabilization device 80, such as a fibroid stabilization screw or tumor screw, and the integral optical device 52a, such as a CMOS imaging sensor or fiber optic imaging device, with an illumination device 98 (FIG. 6). End effector(s) of the second working instrument 40 may include the integral optical device 52a, such as a CMOS imaging sensor or fiber optic imaging device, with the illumination device 98 (FIG. 6), and a cutting device 82, such as a scalpel, electrocautery knife, laser fiber, etc., inserted through a lumen in the second working instrument 40. The cutting device 82 may also be capable of coagulation. The optical devices 52a on both working instruments 30, 40 may be used while performing the following procedure.

The first and second working instruments 30, 40 may be inserted through the vaginal canal VC of the patient. Optionally, the first and second working instruments 30, 40 may be inserted through the guide sheath 20 (FIGS. 2 and 5-9) positioned in the vaginal canal VC.

Then, the surgeon may insert the first working instrument 30 through the cervical canal CC so that the distal end 32 of the first working instrument 30 is located inside the uterine cavity UC at the work site. The work site may include the portion of the wall of body tissue of the uterine cavity UC surrounding and including the uterine fibroid UF to be removed, including portions along both sides of the wall.

The surgeon may rotate the fibroid screw of the stabilization device 80 of the first working instrument 30 into the fibroid UF, e.g., under transabdominal ultrasound guidance, in order to stabilize the fibroid UF while other steps of the procedure described below are performed.

The surgeon may use the cutting device 82 on the second working instrument 40 to create an incision I in the vaginal fornix VF. Then, the surgeon may advance the distal end 42 of the second working instrument 40 through the incision I and toward the work site. Accordingly, the distal end 32 of the first working instrument 30 is disposed inside the uterine cavity UC of the patient, and the distal end 42 of the second working instrument 40 is disposed outside the uterine cavity UC. Also, as shown in FIG. 1, the distal ends 32, 42 of the first and second working instruments 30, 40 may be positioned at opposite sides of the wall of the uterine cavity UC at the work site.

Then, the cutting device 82 of the second working instrument 40 may make an incision in the wall of the uterine cavity UC near the fibroid UF to expose the capsule of the fibroid UF. Once the fibroid UF is exposed, the surgeon may remove the cutting device 82 from the lumen of the second working instrument 40 and replace it with other devices as described below.

For larger fibroids UF, the second working instrument 40 may be used to introduce a morcellating device (not shown) to cut the fibroid UF into smaller pieces. The second working instrument 40 may then be used to introduce a grasping device (not shown) or another fibroid or tumor screw, for fixing onto the fibroid UF. Then, the first working instrument 30 may release the fibroid UF, and the grasping device in the second working instrument 40 may be removed from the second working instrument 40 to remove the fibroid UF from the patient. Next, the grasping device in the second working instrument 40 may be replaced with a suturing device (not shown) to close the incision in the wall of the uterine cavity UC. Then, the suturing device in the second working instrument 40 may be replaced with a device for applying an adhesion barrier, such as a liquid, gel, or mesh, to the suture site.

Then, both the first and second working instruments 30, 40 may be removed from the work site. After the second working instrument 40 is removed from the incision I, the incision I in the vaginal fornix VF may close naturally or using a suturing device introduced by the second working instrument 40.

Figure 2:
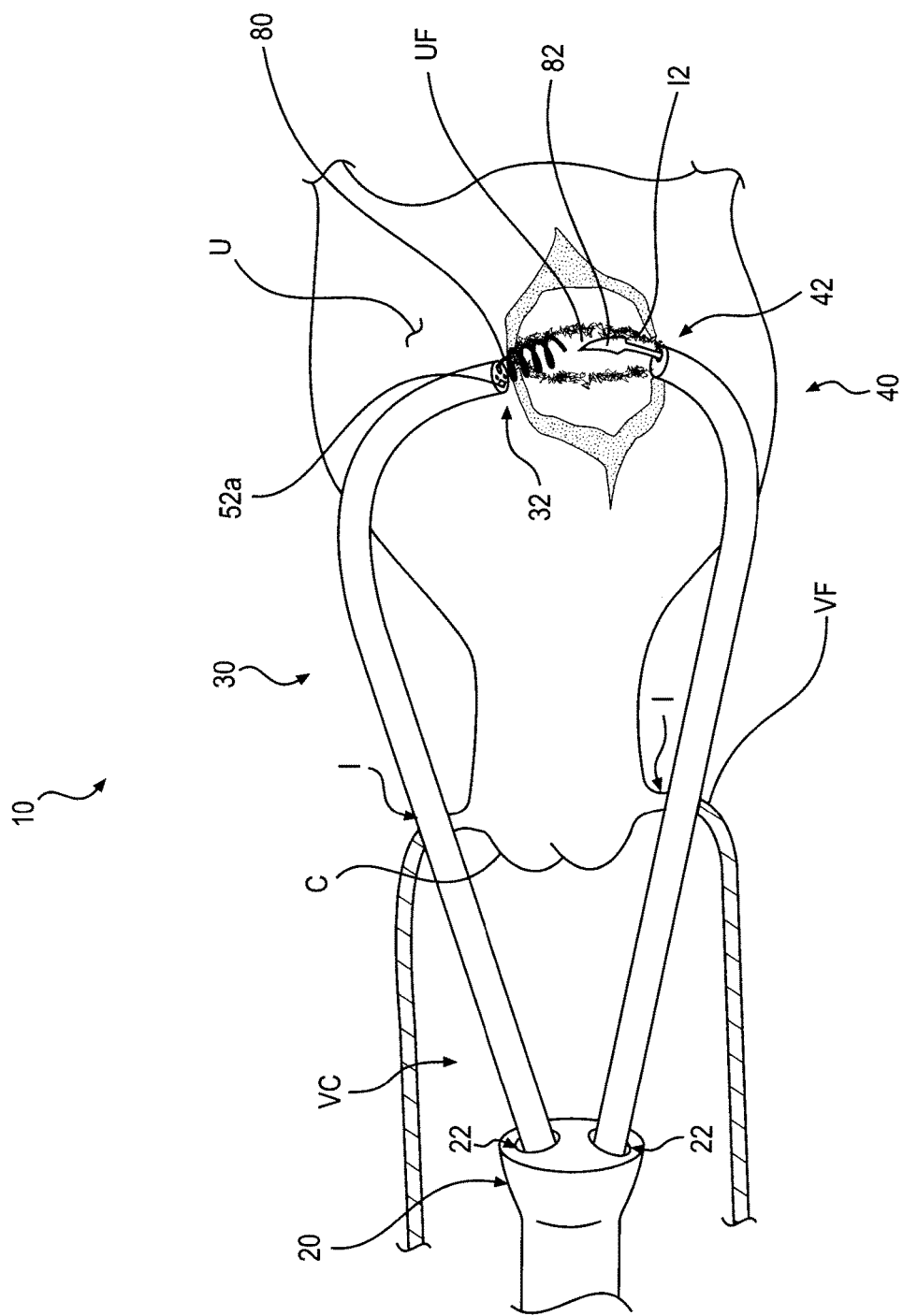
FIG. 2 is a cross-sectional view of a body portion showing a device for performing a myomectomy, the device including two working instruments extending outside the uterine cavity, according to an exemplary embodiment of the invention.

FIG. 2 shows another endoscopic device 10 including the first and second working instruments 30, 40 for performing a myomectomy. The procedure described below may be advantageous for submucosal fibroids. End effector(s) of the first working instrument 30 may include the stabilization device 80 described above in connection with FIG. 1, and the integral optical device 52*a*, such as a CMOS imaging sensor or fiber optic imaging device, with the illumination device 98 (FIG. 6). The optical device 52*a* may be used while performing the procedure described below. End effector(s) of the second working instrument 40 may include the cutting device 82 described above in connection with the embodiment shown in FIG. 1, which may be inserted through a lumen in the second working instrument 40. The first and second working instruments 30, 40 may be extended through the guide sheath 20 positioned in the vaginal canal VC of the patient.

The surgeon may use the cutting device 82 on the second working instrument 40 to create two incisions I in different locations in the vaginal fornix VF. The two incisions I may be located in the vaginal fornix VF, e.g., near opposite sides of the cervix C, as shown in FIG. 2. The two incisions I may be separated by a distance that allows the surgeon to be provided with a wider range of positions with respect to the work site for greater leverage, accessibility, and freedom of movement. For example, the two incisions I may be separated by a distance so that the working instruments 30, 40 extend away from each other as they pass through the incisions I.

The surgeon may advance the distal end 32 of the first working instrument 30 through one of the incisions I and toward the work site, and may advance the distal end 42 of the second working instrument 40 through the other incision I and toward the work site. Accordingly, the distal ends 32, 42 of the first and second working instruments 30, 40 are disposed outside the uterine cavity UC at or near the work site. The work site may include the portion of the wall of body tissue of the uterine cavity UC surrounding and including the uterine fibroid UF to be removed.

At least one or more of the steps of stabilizing the fibroid UF, creating an incision I2 in the wall of the uterus U, exposing the fibroid UF, morcellating the fibroid UF, removing the fibroid UF, closing the incision I2 in the wall of the uterus U, and applying an adhesion barrier to the suture site may be performed as described above in connection with the embodiment shown in FIG. 1. Transabdominal ultrasound guidance may be omitted in this procedure since the fibroid UF may be exposed, stabilized, and removed under direct visualization with the first working instrument 30. For pedunculated fibroids, the stock of the fibroid UF may be surgically cut using a cutting device (e.g., cutting device 82) inserted through the second working instrument 40, and the fibroid UF may be removed through the vaginal fornix VF and/or via morcellation as described above in connection with the embodiment shown in FIG. 1.

Then, both the first and second working instruments 30, 40 may be removed from the work site. After the first and second working instruments 30, 40 are removed from the respective incisions I in the vaginal fornix VF, the incisions I may close naturally or using a suturing device introduced by the second working instrument 40.

Figure 3:
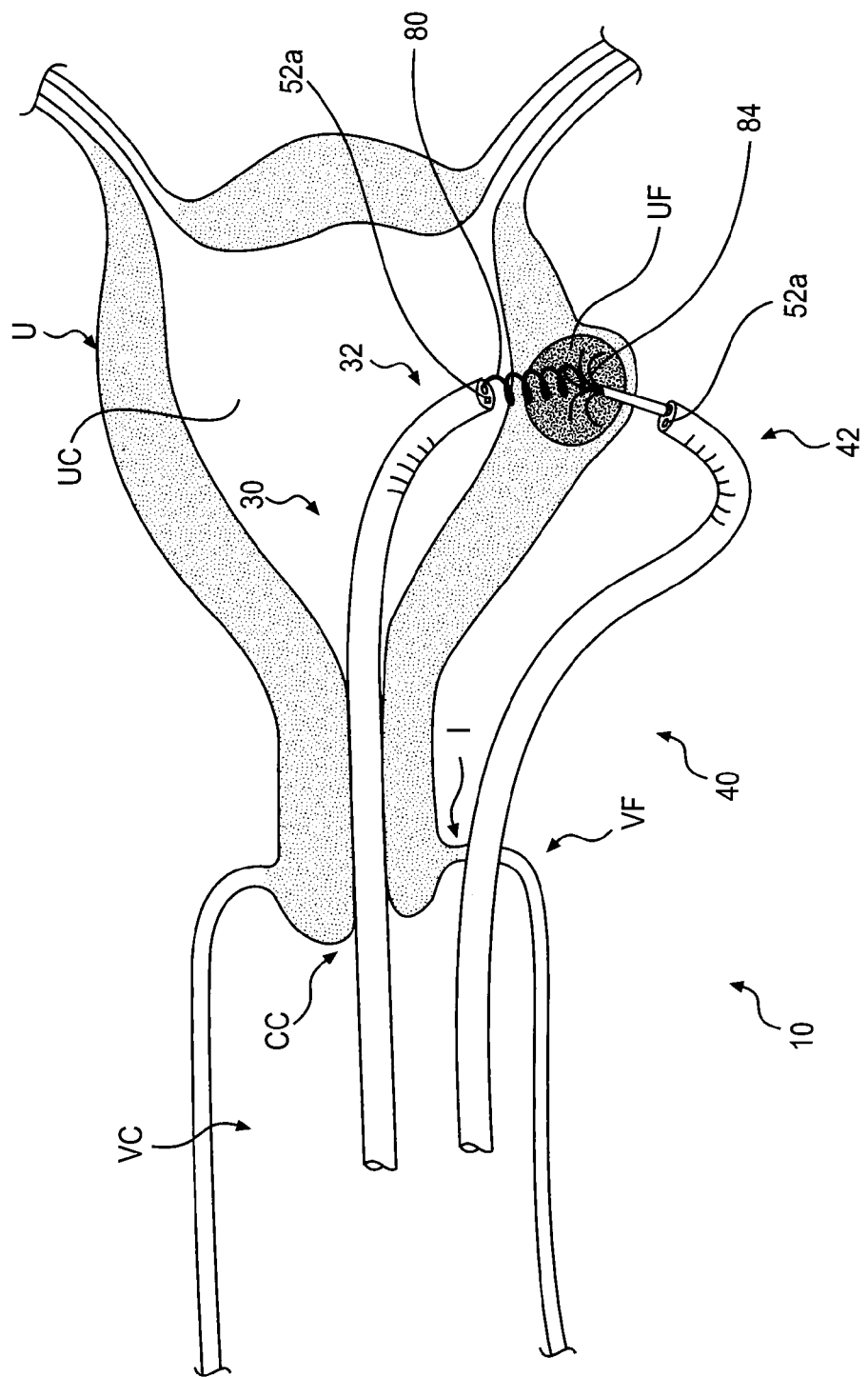
FIG. 3 is a cross-sectional view of a body portion showing a device for performing a uterine fibroid ablation procedure, the device including one working instrument extending into the uterine cavity and another working instrument extending outside the uterine cavity, according to an exemplary embodiment of the invention.

FIG. 3 is shows the endoscopic device 10 for performing a uterine fibroid ablation procedure performed transvaginally. The procedure described below may be advantageous for subserosal and intramural fibroids. End effector(s) of the first working instrument 30 may include the stabilization device 80 described above in connection with the embodiment shown in FIG. 1, and the integral optical device 52*a*, such as a CMOS imaging sensor or fiber optic imaging device with the illumination device 98 (FIG. 6). End effector(s) of the second working instrument 40 may include the integral optical device 52*a*, such as a CMOS imaging sensor or fiber optic imaging device, with the illumination device 98 (FIG. 6), and an ablation device 84 inserted through a lumen in the second working instrument 40. The ablation device 84 may be a radiofrequency (RF) array, LeVeen® needle electrode, or other ablation device using cryo, microwave, laser, vapor, or other ablation methods. The optical devices 52*a* on both working instruments 30, 40 may be used while performing the following procedure.

The first and second working instruments 30, 40 may be inserted through the vaginal canal VC of the patient, optionally using the guide sheath 20 (FIGS. 2 and 5-9). The surgeon may insert the first working instrument 30 through the cervical canal CC so that the distal end 32 of the first working instrument 30 is located inside the uterine cavity UC at the work site and may stabilize the fibroid UF using the stabilization device 80, as described above in connection with the embodiment shown in FIG. 1. The work site may include the portion of the wall of body tissue of the uterine cavity UC surrounding and including the uterine fibroid UF to be removed, including portions along both sides of the wall.

A cutting device (e.g., the cutting device 82) may be inserted into the second working instrument 40 before inserting the ablation device 84 so that the surgeon may create an incision I in the vaginal fornix VF, as described above in connection with the embodiment shown in FIG. 1. Then, the surgeon may advance the distal end 42 of the second working instrument 40 through the incision I and toward the work site, as described above in connection with the embodiment shown in FIG. 1. As shown in FIG. 3, the distal ends 32, 42 of the first and second working instruments 30, 40 may be positioned at opposite sides of the wall of the uterine cavity UC at the work site.

The surgeon may remove the cutting device and replace it with the ablation device 84. The surgeon may use the ablation device 84 to ablate one or more of the patient's fibroids UF to cause necrosis. Then, both the first and second working instruments 30, 40 may be removed from the work site. After the second working instrument 40 is removed from the incision I in the vaginal fornix VF, the incision I may close naturally or using a suturing device introduced by the second working instrument 40 or an additional working instrument.

Figure 4:
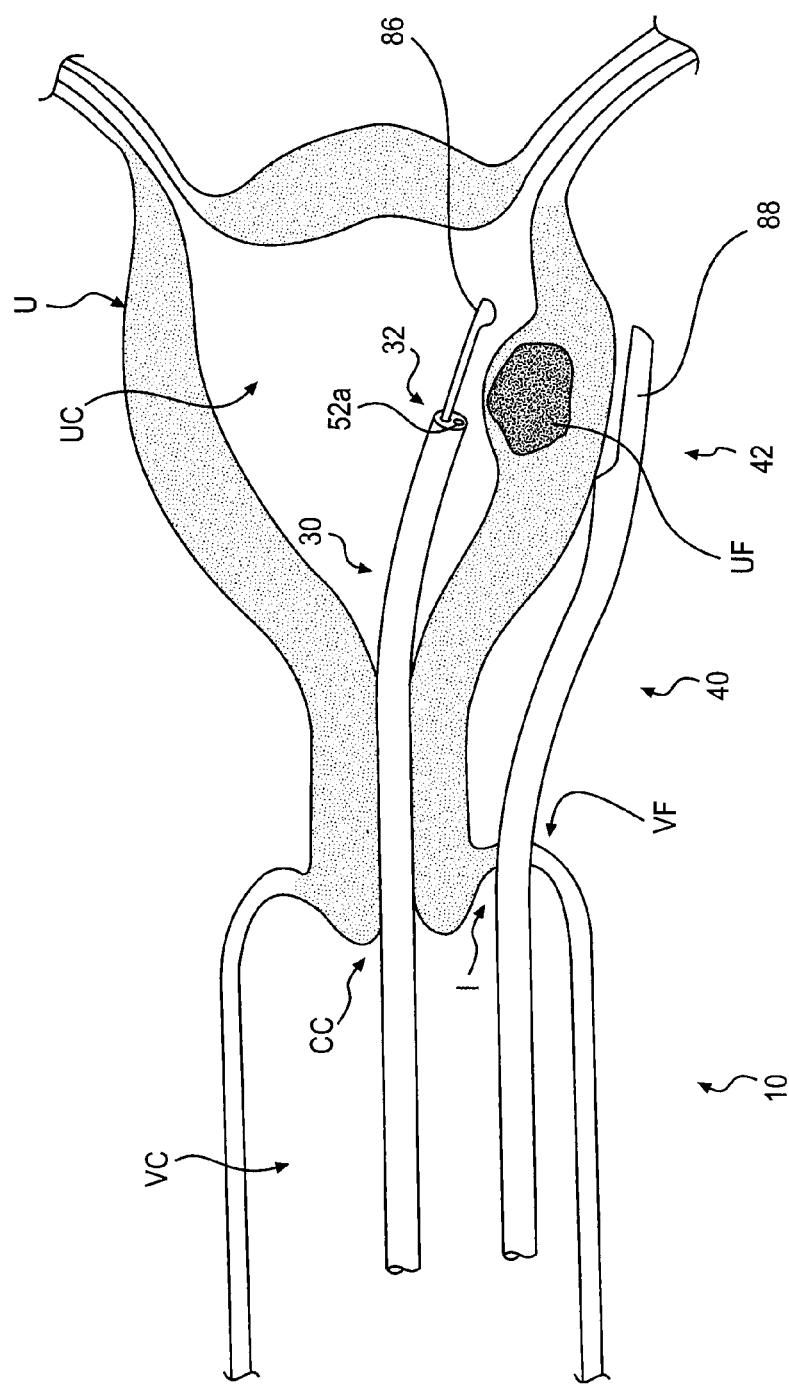
FIG. 4 is a cross-sectional view of a body portion showing a device for treating submucosal uterine fibroids, the device including one working instrument extending into the uterine cavity and another working instrument extending outside the uterine cavity, according to an exemplary embodiment of the invention.

FIG. 4 shows the endoscopic device 10 including first and second working instruments 30, 40 for resecting uterine fibroids. The procedure described below may be advantageous for submucosal uterine fibroids. End effector(s) of the first working instrument 30 may include a resection device 86, such as a resection loop for resecting body tissue, and the integral optical device 52*a*, such as a CMOS imaging sensor or fiber optic imaging device, with the illumination device 98 (FIG. 6). End effector(s) of the second working instrument 40 may also include the integral optical device 52*a*, such as a CMOS imaging sensor or fiber optic imaging device, with the illumination device 98 (FIG. 6), and a pressure application device 88 that is capable of applying external pressure to a wall of body tissue. Alternatively, instead of the optical device, the second working instrument 40 may include a diagnostic ultrasound function that aids in locating the fibroid UF. The optical devices 52a and/or the ultrasound function in the working instruments 30, 40 may be used while performing the following procedure.

The first and second working instruments 30, 40 may be inserted through the vaginal canal VC of the patient, optionally using the guide sheath 20 (FIGS. 2 and 5-9). The surgeon may insert the first working instrument 30 through the cervical canal CC so that the distal end 32 of the first working instrument 30 is located inside the uterine cavity UC at the work site, as described above in connection with the embodiment shown in FIG. 1. The work site may include the portion of the wall of body tissue of the uterine cavity UC surrounding and including the uterine fibroid UF to be resected, including portions along both sides of the wall of the uterine cavity UC.

A cutting device (e.g., the cutting device 82) may be used to create an incision I in the vaginal fornix VF, as described above in connection with the embodiment shown in FIG. 1. The cutting device 82 may be provided using the first or second working instruments 30, 40 (e.g., before inserting the resection device 86 or the pressure application device 88) or may be provided in a separate working instrument (e.g., before or in addition to inserting the first or second working instruments 30, 40 into the patient). Then, the surgeon may remove the cutting device 82 and may advance the distal end 42 of the second working instrument 40 through the incision I and toward the work site, as described above in connection with the embodiment shown in FIG. 1. The surgeon may position the resection device 86 and the pressure application device 88 at opposite sides of the wall of the uterine cavity UC at the work site, as shown in FIG. 4.

Then, the surgeon may use the resection device 86 to shave the patient's fibroid UF, which protrudes into the uterine cavity UC, while using the pressure application device 88 to apply external pressure (e.g., applying a vacuum or other pressurized fluid flow) to the wall of the uterine cavity UC to increase the area of the fibroid UF that is exposed for resection.

Then, both the first and second working instruments 30, 40 may be removed from the work site. After the second working instrument 40 is removed from the incision I, the incision I in the vaginal fornix VF may close naturally or using a suturing device introduced by one of the working instruments 30, 40 or an additional working instrument.

Figure 5:
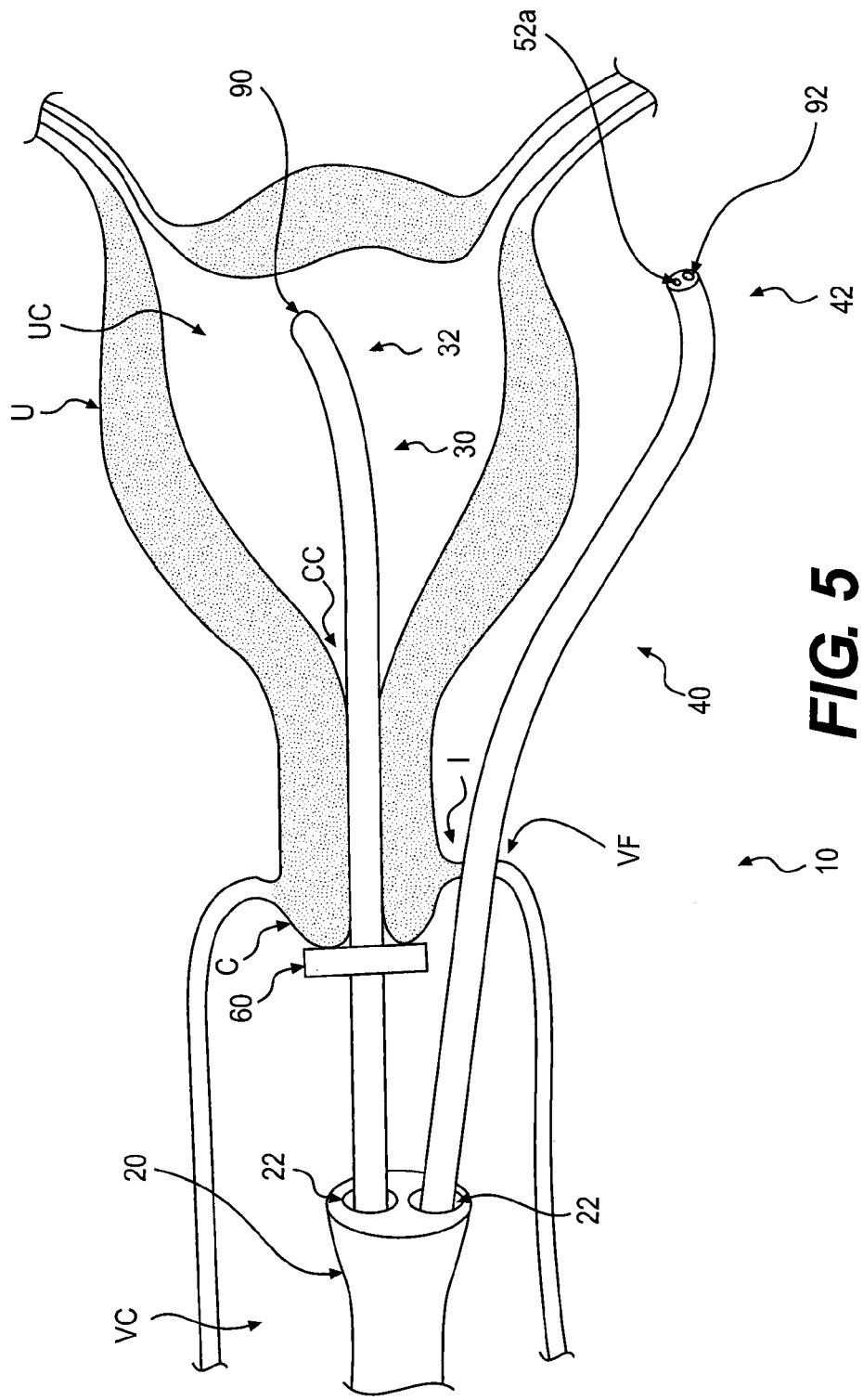
FIG. 5 is a cross-sectional view of a body portion showing a device for treating endometriosis, the device including one working instrument extending into the uterine cavity and another working instrument extending outside the uterine cavity, according to an exemplary embodiment of the invention.

FIG. 5 shows the endoscopic device 10 including first and second working instruments 30, 40 for treating endometriosis. End effector(s) of the first working instrument 30 may include a manipulation device 90, such as a device capable of moving body tissue. For example, the manipulation device 90 may include a blunt tip or may apply pressure to move body tissue. End effector(s) of the second working instrument 40 may include the integral optical device 52a, such as a CMOS imaging sensor or fiber optic imaging device, with the illumination device 98 (FIG. 6), and an energy delivery device 92 that is configured to apply energy, e.g., for coagulation. For example, the energy delivery device 92 may deliver sufficient radiofrequency, laser, plasma, cryo, or ultrasound energy to destroy the endometriosis lesions. The optical device 52a may be used while performing the following procedure.

The first and second working instruments 30, 40 may be extended through the guide sheath 20 positioned in the vaginal canal VC of the patient. Then, the surgeon may insert the first working instrument 30 through the cervical canal CC so that the distal end 32 of the first working instrument 30 is located inside the uterine cavity UC at the work site, as described above in connection with the embodiment shown in FIG. 1. The work site may include the portion of the wall of body tissue of the uterine cavity UC surrounding and including the portion with endometriosis lesions and the portion to be manipulated to expose the endometriosis lesions, including portions along both sides of the wall of the uterine cavity UC.

The first working instrument 30 may include the positioning device or collar 60 having a diameter that is larger than the diameter of the cervical canal CC and including a distal face that is configured to abut the cervix C. Setting the position of the collar 60 on the first working instrument 30 allows the surgeon to set the distance that the distal end 32 of the first working instrument 30 may be inserted into the uterine cavity UC, thereby preventing the surgeon from inserting the first working instrument 30 too far into the uterine cavity UC.

A cutting device (e.g., the cutting device 82) may be used to create an incision I in the vaginal fornix VF, as described above in connection with the embodiment shown in FIG. 1. The cutting device 82 may be provided using the first or second working instruments 30, 40 (e.g., inserted into the second working instrument 40 before inserting the energy delivery device 92) or may be provided in a separate working instrument (e.g., before or in addition to inserting the first or second working instruments 30, 40). Then, the surgeon may remove the cutting device 82 and may advance the distal end 42 of the second working instrument 40 through the incision I and toward the work site, as described above in connection with the embodiment shown in FIG. 1. The distal ends 32, 42 of the first and second working instruments 30, 40 may be positioned at opposite sides of the wall of the uterine cavity UC at the work site, as shown in FIG. 5.

The surgeon may use the energy delivery device 92 to coagulate endometriosis lesions while using the optical device 52a to locate the endometriosis lesions and using the manipulation device 90 to move at least portions of the uterus to expose the endometriosis lesions.

Then, both the first and second working instruments 30, 40 may be removed from the work site. After the second working instrument 40 is removed from the incision I, the incision I in the vaginal fornix VF may close naturally or using a suturing device introduced by one of the working instruments 30, 40 or an additional working instrument.

FIG. 6 shows another endoscopic device 10 including first and second working instruments 30, 40 for treating endometriosis. End effector(s) of the first working instrument 30 may include the integral optical device 52a, such as a CMOS imaging sensor or fiber optic imaging device, with the illumination device 98. End effector(s) of the second working instrument 40 may include the energy delivery device 92 that applies energy, e.g., for coagulation. The optical device 52a may be used while performing the following procedure.

The first and second working instruments 30, 40 may be extended through the guide sheath 20 positioned in the vaginal canal VC of the patient. A cutting device (e.g., the cutting device 82) may be used to create two incisions I in different locations in the vaginal fornix VF, as described above in connection with the embodiment shown in FIG. 2. The two incisions I may be located in the vaginal fornix VF, e.g., near opposite sides of the cervical canal CC, as shown in FIG. 6. The cutting device 82 may be provided using the first or second working instruments 30, 40 or may be provided in a separate working instrument (e.g., before or in addition to inserting the first or second working instruments 30, 40 into the patient).

The surgeon may advance the distal end 32 of the first working instrument 30 through one of the incisions I and toward the work site, and may advance the distal end 42 of the second working instrument 40 through the other incision I and toward the work site. Accordingly, the distal ends 32, 42 of the first and second working instruments 30, 40 are disposed outside the uterus U at the work site. The work site may include the portion of the wall of body tissue surrounding and including the endometriosis lesions L outside the uterus U.

The surgeon may use the energy delivery device 92 to coagulate the endometriosis lesions L. Then, both the first and second working instruments 30, 40 may be removed from the work site. After the first and second working instruments 30, 40 are removed from the respective incisions I, the incisions I in the vaginal fornix VF may close naturally or using a suturing device provided using the first or second working instruments 30, 40 or an additional working instrument.

Figure 7:
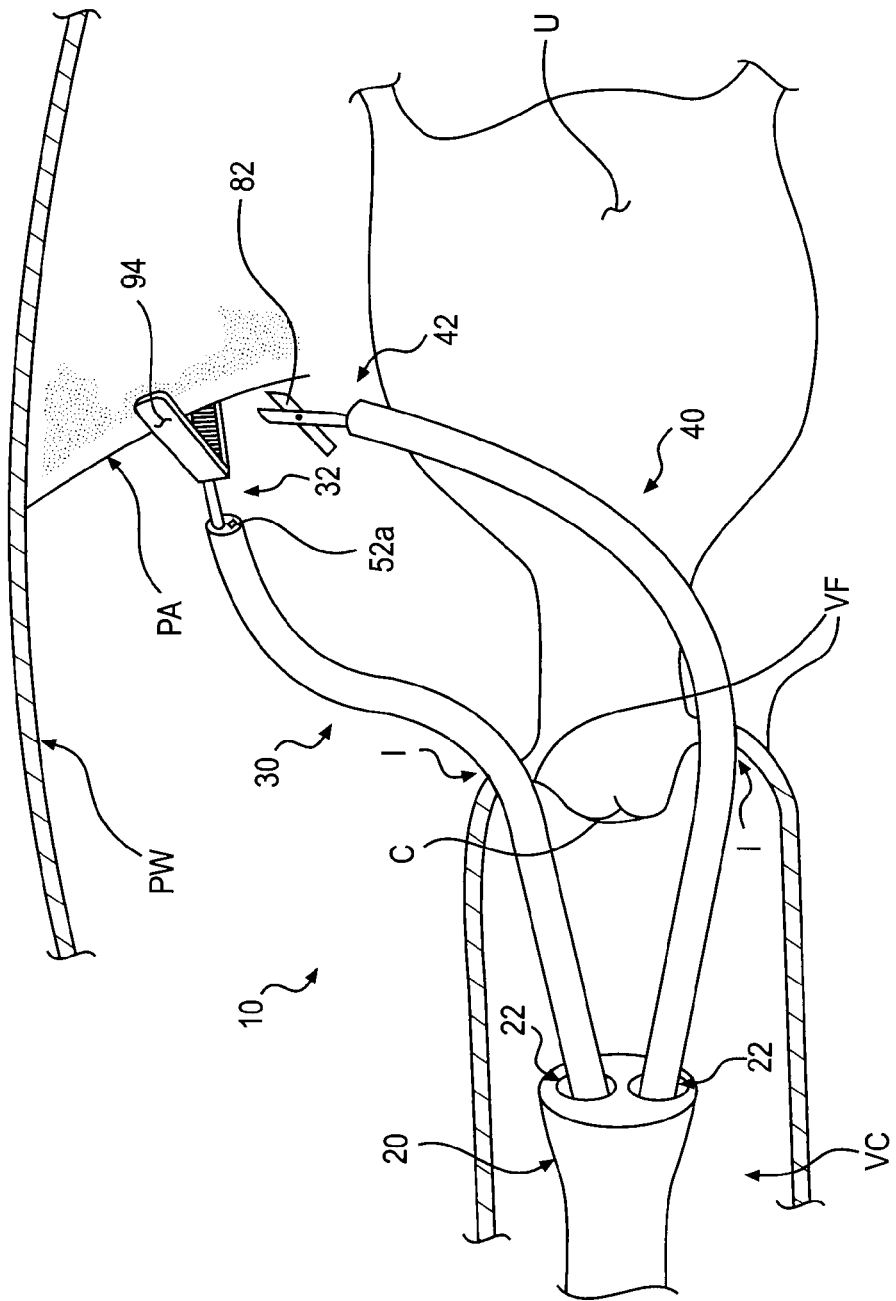
FIG. 7 is a cross-sectional view of a body portion showing a device for treating adhesions in the pelvic area, the device including two working instruments extending outside the uterine cavity and into the pelvic area, according to an exemplary embodiment of the invention.

FIG. 7 shows an endoscopic device 10 including first and second working instruments 30, 40 for treating adhesions PA in the pelvic area. End effector(s) of the first working instrument 30 may include the integral optical device 52a, such as a CMOS imaging sensor or fiber optic imaging device, with the illumination device 98 (FIG. 6), and a grasping device 94 configured to grasp body tissue. End effector(s) of the second working instrument 40 may include the cutting device 82, such as the cutting device described above in connection with the embodiment shown in FIG. 1. The optical device 52a may be used while performing the following procedure.

The first and second working instruments 30, 40 may be extended through the guide sheath 20 positioned in the vaginal canal VC of the patient. The cutting device 82 may be used to create two incisions I in different locations in the vaginal fornix VF. The two incisions I may be located in the vaginal fornix VF, e.g., near opposite sides of the cervical canal CC, as shown in FIG. 7.

The surgeon may advance the distal end 32 of the first working instrument 30 through one of the incisions I and toward the work site, and may advance the distal end 42 of the second working instrument 40 through the other incision I and toward the work site. Accordingly, the distal ends 32, 42 of the first and second working instruments 30, 40 are disposed outside the uterine cavity UC at or near the work site in the pelvic area. The work site may surround and include the adhesions PA in the pelvic area. The adhesions PA may extend from a pelvic side wall PW, as shown in FIG. 7.

The surgeon may use the grasping device 94 of the first working instrument 30 to grasp or hold the adhesion PA while the adhesion PA is cut by the cutting device 82 of the second working instrument 40. The grasping device 94 may also be used to remove cut tissue. After cutting the tissue, the surgeon may remove the cutting device 82 from the lumen in the second working instrument 40 and may insert a device for delivering an adhesion barrier, such as a liquid, gel, or mesh, to the pelvic area.

Then, both the first and second working instruments 30, 40 may be removed from the work site. After the first and second working instruments 30, 40 are removed from the respective incisions I, the incisions I in the vaginal fornix VF may close naturally or using a suturing device provided using the first or second working instruments 30, 40 (e.g., inserted through the respective lumen in the first or second working instrument 30, 40 after removing the grasping device 94 or the cutting device 82) or in an additional working instrument.

Figure 8:
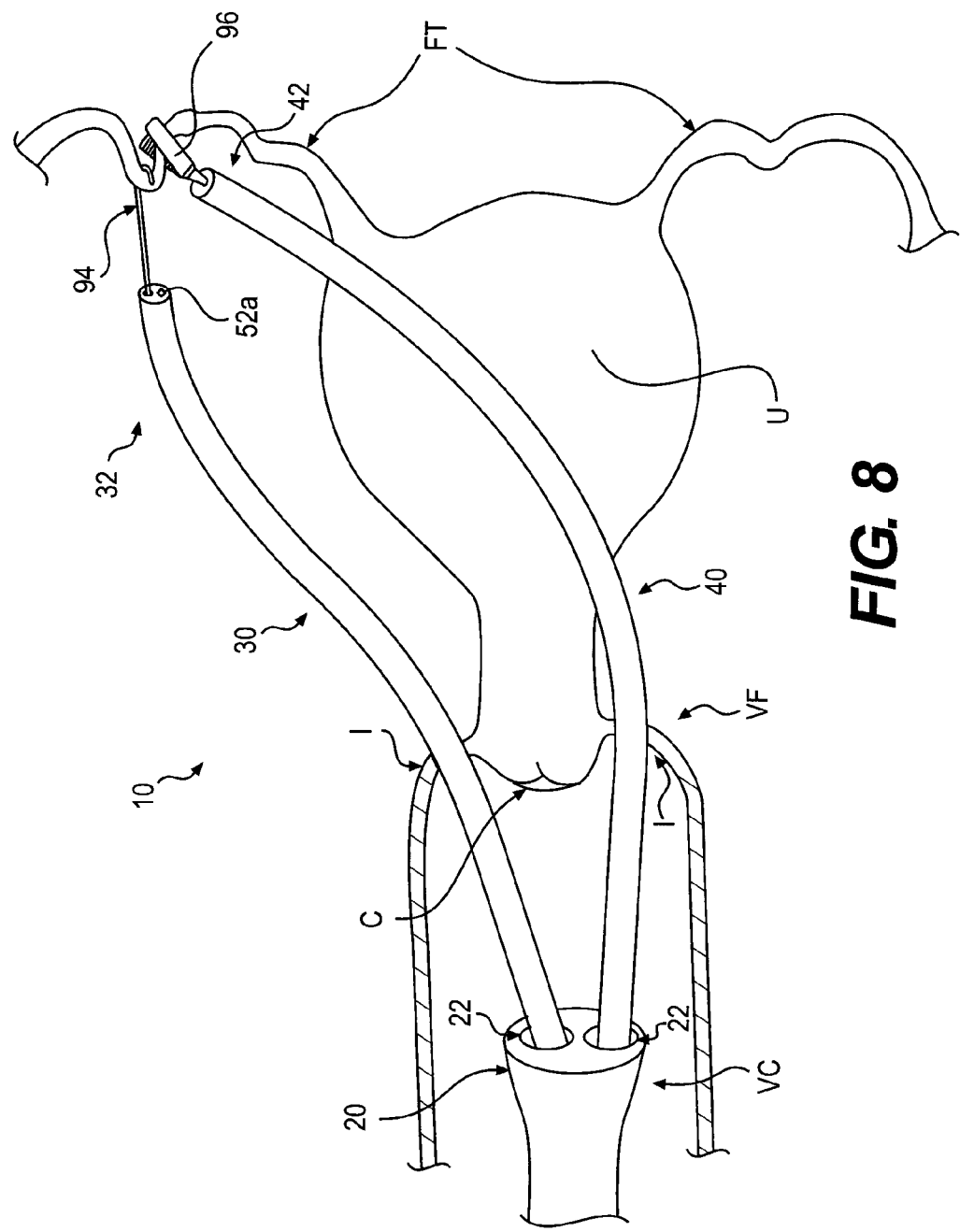
FIG. 8 is a cross-sectional view of a body portion showing a device for performing female sterilization, the device including two working instruments extending outside the uterine cavity and toward a fallopian tube, according to an exemplary embodiment of the invention.

FIG. 8 shows an endoscopic device 10 including first and second working instruments 30, 40 for performing female sterilization. End effector(s) of the first working instrument 30 may include the grasping device 94 configured to grasp body tissue, such as the grasping device described above in connection with the embodiment shown in FIG. 7, and the integral optical device 52a, such as a CMOS imaging sensor or fiber optic imaging device, with the illumination device 98 (FIG. 6). End effector(s) of the second working instrument 40 may include a ligation device 96 configured to ligate a tube. For example, the ligation device 96 may include, but is not limited to, a clip, suture, loop, staple, coagulating device, cutting and coagulation device, etc. The optical device 52a may be used while performing the following procedure.

The first and second working instruments 30, 40 may be extended through the guide sheath 20 positioned in the vaginal canal VC of the patient. A cutting device (e.g., the cutting device 82) may be used to create two incisions I in different locations in the vaginal fornix VF, as described above in connection with the embodiment shown in FIG. 2. The two incisions I may be located in the vaginal fornix VF, e.g., near opposite sides of the cervical canal CC, as shown in FIG. 8. The cutting device 82 may be provided using the first or second working instruments 30, 40 (e.g., inserted through the respective lumen in the first or second working instrument 30, 40 before inserting the grasping device 94 or the ligation device 96) or may be provided in a separate working instrument (e.g., before or in addition to inserting the first or second working instruments 30, 40 into the patient).

The surgeon may advance the distal end 32 of the first working instrument 30 through one of the incisions I and toward the work site, and may advance the distal end 42 of the second working instrument 40 through the other incision I and toward the work site. Accordingly, the distal ends 32, 42 of the first and second working instruments 30, 40 are disposed outside the uterus U at the work site. The work site may include the portions of the fallopian tubes FT surrounding and including the portions to be grasped and/or ligated.

After using the grasping device 94 or the ligation device 96 to ligate the fallopian tubes FT, both the first and second working instruments 30, 40 may be removed from the work site. After the first and second working instruments 30, 40 are removed from the respective incisions I, the incisions I in the vaginal fornix VF may close naturally or using a suturing device provided using the first or second working instruments 30, 40 (e.g., inserted through the respective lumen in the first or second working instrument 30, 40 after removing the grasping device 94 or the ligation device 96) or in an additional working instrument.

Figure 9:
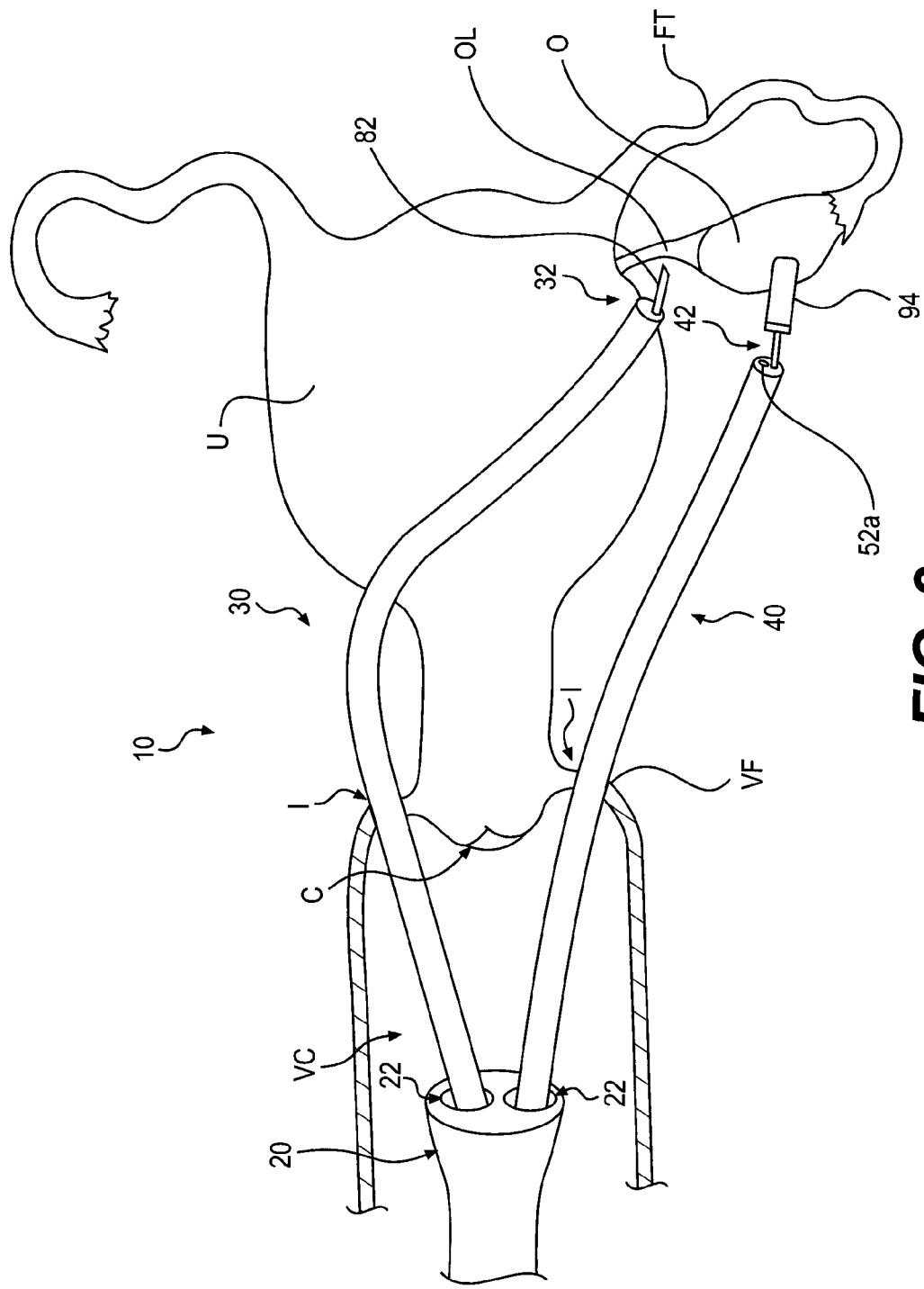
FIG. 9 is a cross-sectional view of a body portion showing a device for treating diseases of the adnexal mass, the device including two working instruments extending outside the uterine cavity and toward an ovary, according to an exemplary embodiment of the invention.

FIG. 9 shows an endoscopic device 10 including first and second working instruments 30, 40 for treating diseases of the adnexal mass (e.g., the ovaries, fallopian tubes, ovary ligaments, and/or uterine ligaments). End effector(s) of the first working instrument 30 may include the cutting device 82, such as the cutting device described above in connection with the embodiment shown in FIG. 1. End effector(s) of the second working instrument 40 may include the integral optical device 52a, such as a CMOS imaging sensor or fiber optic imaging device, with the illumination device 98 (FIG. 6), and the grasping device 94 configured to grasp body tissue, such as the grasping device described above in connection with the embodiment shown in FIG. 7. The optical device 52a may be used while performing the following procedure.

The first and second working instruments 30, 40 may be extended through the guide sheath 20 positioned in the vaginal canal VC of the patient. The cutting device 82 may be used to create two incisions I in different locations in the vaginal fornix VF. The two incisions I may be located in the vaginal fornix VF, e.g., near opposite sides of the cervical canal CC, as shown in FIG. 9.

The surgeon may advance the distal end 32 of the first working instrument 30 through one of the incisions I and toward the work site, and may advance the distal end 42 of the second working instrument 40 through the other incision I and toward the work site. Accordingly, the distal ends 32, 42 of the first and second working instruments 30, 40 are disposed outside the uterus U at or near the work site. The work site may surround and include the portions of the ovaries O (e.g., ovarian cysts), fallopian tubes FT, and/or uterine or ovary ligaments OL to be grasped, cut, and/or otherwise treated.

The surgeon may use the grasping device 94 of the second working instrument 40 to grasp or hold body tissue while the body tissue (e.g., some or all of one or both ovaries, ovarian cysts, etc.) is cut by the cutting device 82 of the first working instrument 30. The grasping device 94 may also be used to remove the cut tissue. After cutting the tissue, the surgeon may remove the cutting device 82 from the lumen in the first working instrument 30 and may insert a suturing device for suturing to close any incisions in the work site, an irrigation device to irrigate the work site, a suction device to remove any tissue or fluids from the work site, and/or a device for delivering an adhesion barrier, such as a liquid, gel, or mesh, to the work site.

Then, both the first and second working instruments 30, 40 may be removed from the work site. After the first and second working instruments 30, 40 are removed from the respective incisions I, the incisions I in the vaginal fornix VF may close naturally or using a suturing device provided using the first or second working instruments 30, 40 (e.g., inserted through the respective lumen in the first or second working instrument 30, 40 after removing the grasping device 94 or the cutting device 82) or in an additional working instrument.

In various embodiments described above, multiple working instruments 30, 40 may be located at or near the same work site and may be used in concert to perform different functions at the same work site in a less invasive procedure. The endoscopic device 10 may also be used for intracavitary and/or extracavitary procedures in or near various body organs, such as the uterus, bladder, stomach, esophagus, intestine or other organs in the lower gastrointestinal tract, heart, etc.

In various embodiments, the endoscopic device 10 may include the first working instrument 30 that may extend inside a body organ and the second working instrument 40 that may extend outside the same body organ. The two working instruments 30, 40 may enter the patient's body organ through a natural orifice and/or through a minimally invasive incision, and may be used in concert to perform opposing or complimentary functions to complete a medical procedure.

For example, one working instrument 30, 40 may access the work site through a natural orifice, and the other working instrument 30, 40 may access the work site through a minimally invasive incision I. For example, as shown in FIGS. 1, 3-5, 10, and 11, the distal end 32 of the first working instrument 30 may be inserted into a body organ (e.g., the uterus) through a natural orifice (e.g., the vagina and the cervical canal). The distal end 42 of the second working instrument 40 may be inserted through a natural orifice (e.g., the vagina), inserted through a minimally invasive incision I (e.g., in the vaginal fornix VF), and positioned outside the same body organ (e.g., the uterus) at the same work site on opposite sides of a wall of the body organ from the first working instrument 30 to perform a procedure in concert with the first working instrument 30 at that work site. The endoscopic device 10 may then perform an intracavitary (inside a body cavity) procedure at the work site.

Alternatively, both working instruments 30, 40 may enter through a natural orifice and minimally invasive incisions I. For example, as shown in FIGS. 2 and 6-9, the distal ends 32, 42 of the first and second working instruments 30, 40 may be inserted through a natural orifice (e.g., the vagina), inserted through separate minimally invasive incisions I (e.g., in the vaginal fornix VF), and positioned at the same work site (e.g., outside the uterus, in the pelvic area, at a fallopian tube, at an ovary, at ovary or uterine ligaments, etc.) to perform a procedure in concert with the first working instrument 30 at that work site. The endoscopic device 10 may then perform an extracavitary (outside a body cavity) procedure at the work site. Also, the first and second working instruments 30, 40 may be inserted through opposing sides of the vaginal fornix VF near opposite sides of the cervix C (or through two other spaced apart incisions I), thereby causing the working instruments 30, 40 to diverge away from each other, e.g., at an angle A (FIG. 6). Since the working instruments 30, 40 diverge, the working instruments 30, 40 may provide improved triangulation. Providing "pop-up" end effectors as described above also allows the surgeon to position the end effectors to diverge away from each other, thereby also providing improved triangulation.

By having the working instruments 30, 40 approach the same work site from different paths and/or incisions as described above, the surgeon is provided with a larger range of view using the optical device(s) 52a, 52b and illumination device(s) 98. For example, the optical device 52a, 52b on one working instrument 30, 40 may be positioned at a location that provides more of a "bird's eye view" with respect to the work site and the other working instrument 30, 40. Also, the surgeon is able to position the working instruments 30, 40 along a wider range of positions with respect to the work site for greater leverage, accessibility, and freedom of movement.

In some embodiments, one or more of the working instruments 30, 40 may include both the illumination device 98 and the optical device 52a, 52b independently, and images from these devices can be projected or displayed side by side on the same screen to the surgeon. Providing illumination and visualization independently on each working instrument 30, 40 allows for the transmission of more detail of the work site. The signals from both working instruments 30, 40 may be merged using software to provide a more detailed field of view. Also, a three-dimensional image may be provided using the multiple signals.

In any of the embodiments described above, additional working instruments may be extended, e.g., through the guide sheath 20 or separately from the guide sheath 20, and positioned at the work site in addition to the first and second working instruments 30, 40. For example, one or more additional working instruments may include any of the end effectors 50 described above, such as the optical device 52a, 52b. The additional working instruments may be inserted through the cervical canal CC with the first working instrument 30, through the incision(s) I in the vaginal fornix VF with the first or second working instruments 30, 40, or through other incisions (e.g., in the vaginal fornix VF or at another location in the vaginal wall). The additional incision may be located so that the additional working instrument may approach the work site from a path that is different from the first and second working instruments 30, 40. As a result, the working instrument may provide a different view of the work site (if the working instrument includes the optical device 52a, 52b), and/or the surgeon may be able to position the working instrument within a range of positions that is different from the ranges available using the first and second working instruments 30, 40.

Every endoscopic device 10 set forth herein may be made of a suitable biocompatible material and may be flexible or malleable, for example, to traverse tortuous anatomy in the body. Any aspect set forth in any embodiment may be used with any other embodiment set forth herein. Every device and method set forth herein may be used in any suitable medical procedure, may be advanced through any suitable body organ and body cavity.

It will be apparent to those skilled in the art that various modifications and variations can be made in the disclosed devices and methods without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

In some embodiments, a method of performing a medical procedure in a patient may include inserting a first working instrument and a second working instrument through an opening in the patient, creating an incision in body tissue inside the patient using at least one of the first and second working instruments, and advancing the second working instrument through the incision to position the second working instrument at a work site inside the patient. The method may also include positioning the first working instrument at the work site without advancing the first working instrument through the incision, and performing a procedure at the work site inside the patient using the first and second working instruments.

In some embodiments, the opening through which the first and second working instruments are inserted may be a natural orifice in the patient.

In some embodiments, the opening in the patient may be one of a mouth, a rectum, an anus, a nose, a urethra, an umbilicus, and a vagina of the patient.

In some embodiments, the opening in the patient may be an incision in skin of the patient.

In some embodiments, the method may further include advancing the first working instrument to the work site without creating an incision in body tissue inside the patient to insert the first working instrument.

In some embodiments, positioning the first and second working instruments at the work site may include positioning the first and second working instruments near opposite sides of a wall of body tissue at the work site.

In some embodiments, the work site may be at least part of a body organ of the patient, one of the first working instrument and the second working instrument may be positioned inside the body organ, and the other one of the first working instrument and the second working instrument may be positioned outside the body organ.

In some embodiments, the body organ may be a uterus, a bladder, a stomach, an esophagus, an intestine, an organ in the lower gastrointestinal tract, or a heart.

In some embodiments, the method may further include inserting the first working instrument through a natural orifice opening into the body organ of the patient so that a distal end of the first working instrument may be positioned inside the body organ of the patient at the work site, and a distal end of the second working instrument may be positioned outside the body organ of the patient at the work site.

In some embodiments, the natural orifice opening into the body organ may include a cervical canal of the patient, the distal end of the first working instrument may be positioned inside a uterine cavity at the work site, and the distal end of the second working instrument may be positioned outside the uterine cavity at the work site.

In some embodiments, the incision may be a second incision, and the method may further include creating a first incision in body tissue in the patient, and advancing the first working instrument through the first incision to position the first working instrument at the work site, without advancing the second working instrument through the first incision.

In some embodiments, the first and second working instruments may be advanced through the respective first and second incisions so that the first and second working instruments extend away from each other when extending through the incisions.

In some embodiments, the work site may include tissue of at least one of a uterus, an ovary, a fallopian tube, an ovary ligament, a uterine ligament, and tissue located in a pelvic area.

In some embodiments, the method may further include inserting a guide sheath into the patient, and the first and second working instruments may extend through at least one lumen in the guide sheath.

In some embodiments, the method may further include transmitting at least one image signal using at least one optical device located at a distal end of at least one of the first and second working instruments.

In some embodiments, a first image signal may be transmitted using a first optical device located at the distal end of the first working instrument; and a second image signal may be transmitted using a second optical device located at the distal end of the second working instrument.

In some embodiments, the method may further include providing illumination using an illumination device disposed on each of the distal ends of the first and second working instruments.

In some embodiments, the method may further include creating a three-dimensional image using the first and second image signals.

In some embodiments, the at least one optical device may be independently moveable with respect to the distal end of the at least one first and second working instruments.

In some embodiments, the method may further include connecting distal ends of the first and second working instruments together when the distal ends of the first and second working instruments are inside the patient.

In some embodiments, the first and second working instruments may be independently movable longitudinally, rotationally, and laterally with respect to each other.

In some embodiments, a method of performing a medical procedure in a patient may include inserting a first working instrument and a second working instrument through an opening in the patient, creating an incision in body tissue inside the patient using at least one of the first and second working instruments, and advancing the second working instrument through the incision to position the second working instrument at a work site inside the patient. The method may also include positioning the first and second working instruments near opposite sides of a wall of body tissue at the work site, and performing a procedure at the work site inside the patient using the first and second working instruments.

In some embodiments, the incision may be located in a wall of a body cavity.

In some embodiments, the body cavity may include a vaginal canal, a cervical canal, and a uterine cavity.

In some embodiments, the first and second working instruments may be inserted through a vagina of the patient; the incision created in the body tissue may be an incision in a vaginal wall in the patient; and the wall of body tissue may include a wall of a uterine cavity of the patient.

In some embodiments, the method may further include transmitting a first image signal using a first optical device located at a distal end of the first working instrument; and transmitting a second image signal using a second optical device located at a distal end of the second working instrument.

In some embodiments, the method may further include connecting distal ends of the first and second working instruments together when the distal ends of the first and second working instruments are positioned near the opposite sites of the wall of body tissue at the work site.

In some embodiments, a method of performing a medical procedure in a patient may include inserting a first working instrument and a second working instrument through an opening in the patient, creating a first incision in body tissue at a first location inside the patient using at least one of the first and second working instruments, and creating a second incision in body tissue at a second location inside the patient using at least one of the first and second working instruments. The first and second locations may be different locations. The method may also include advancing the first working instrument through the first incision, advancing the second working instrument through the second incision, and performing a procedure at a work site inside the patient using the first and second working instruments after advancing the first and second working instruments through the respective first and second incisions.

In some embodiments, the method may further include inserting a guide sheath into the patient, and inserting the first and second working instruments at least partially into the guide sheath.

In some embodiments, the first and second working instruments may be advanced through the respective first and second incisions so that the first and second working instruments extend away from each other when extending through the incisions.

In some embodiments, the first and second incisions may be located in a wall of a body cavity.

In some embodiments, the work site may be located outside the body cavity.

In some embodiments, a method of performing a medical procedure in or near a uterus of a patient may include advancing a first working instrument and a second working instrument through a vagina of the patient, creating an incision in a vaginal wall in the patient using at least one of the first and second working instruments, and advancing the second working instrument through the incision to position the second working instrument at a work site on or near the uterus. The method may also include positioning the first working instrument at the work site without advancing the first working instrument through the incision, and performing a procedure at the work site using the first and second working instruments.

In some embodiments, the method may further include advancing the first working instrument to the work site without creating an incision in body tissue inside the patient to insert the first working instrument.

In some embodiments, the method may further include advancing the first working instrument through a cervical canal of the patient so that a distal end of the first working instrument is positioned inside a uterine cavity at the work site, and a distal end of the second working instrument may be positioned outside the uterine cavity at the work site.

In some embodiments, the incision may be located in the vaginal fornix.

In some embodiments, positioning the first and second working instruments at the work site may include positioning the first and second working instruments near opposite sides of a wall of a uterine cavity of the patient at the work site.

In some embodiments, the incision may be a second incision, and the method may further include creating a first incision in the vaginal wall and advancing the first working instrument through the first incision to position the first working instrument at the work site without advancing the second working instrument through the first incision.

In some embodiments, the first and second incisions may be located in different locations in the vaginal fornix.

In some embodiments, a device for performing a medical procedure in a patient may include a first working instrument including a distal end and a second working instrument including a distal end. The first and second working instruments may be configured to move independently from each other. The device may also include a connecting mechanism at the first and second distal ends of the first and second working instruments. The connecting mechanism may be configured to secure the distal end of the first working instrument to the distal end of the second working instrument when the distal ends of the first and second working instruments are disposed inside the patient.

In some embodiments, the connecting mechanism may include a first element on the first working instrument, and the first element may be configured to engage with a second element on the second working instrument.

In some embodiments, one of the first and second elements may include a hook, and the other one of the first and second elements may include a loop.

In some embodiments, the first and second working instruments may be independently movable longitudinally, rotationally, and laterally with respect to each other.

What is claimed is:

1. A method of performing a medical procedure in a patient, the method comprising:
    inserting a first working instrument and a second working instrument through a same opening in the patient, each of the first working instrument and the second working instrument defining a lumen;
    advancing a cutting device through the lumen of the first working instrument or the second working instrument and creating an incision in body tissue inside the patient using the cutting device;
    advancing the second working instrument through the incision and into a first body cavity to position the second working instrument at a first portion of a work site inside the patient;
    advancing the first working instrument through a second body cavity to a second portion of the work site different from the first portion, without advancing the first working instrument through the incision; and performing a procedure at the work site inside the patient using the first and second working instruments by manipulating tissue between the first and second working instruments;

wherein a distal end of the second working instrument advances into the first body cavity without the distal end of the second working instrument advancing into the second body cavity.

2. The method of claim 1, wherein the opening through which the first and second working instruments are inserted is a natural orifice in the patient chosen from a mouth, a rectum, an anus, a nose, a urethra, an umbilicus, and a vagina.

3. The method of claim 1, wherein the opening in the patient is an incision in skin of the patient.

4. The method of claim 1, further including advancing the first working instrument past the opening and through a natural orifice into the second body cavity to reach the work site.

5. The method of claim 1, wherein:
a body organ of the patient includes the work site; and
the procedure is performed with a distal end of one of the first working instrument and the second working instrument positioned inside the body organ, and a distal end of the other one of the first working instrument and the second working instrument positioned outside the body organ.

6. The method of claim 5, further including:
inserting the first working instrument through a natural orifice opening into the body organ of the patient so that the distal end of the first working instrument is positioned inside the body organ of the patient at the work site and the distal end of the second working instrument is positioned outside the body organ of the patient at the work site.

7. The method of claim 1, wherein the incision is a second incision; and the method further includes:
creating a first incision in body tissue in the patient with the cutting device; and
advancing the first working instrument through the first incision to position the first working instrument at the work site, without advancing the second working instrument through the first incision.

8. The method of claim 1, further including inserting a guide sheath into the patient, the first and second working instruments extending through at least one lumen in the guide sheath.

9. The method of claim 1, further including transmitting at least one image signal using at least one optical device located at a distal end of at least one of the first and second working instruments.

10. The method of claim 9, wherein transmitting the at least one image signal includes transmitting a first image signal using a first optical device located at the distal end of the first working instrument and transmitting a second image signal using a second optical device located at the distal end of the second working instrument, the method further comprising creating a three-dimensional image using the first and second image signals.

11. The method of claim 9, further including illuminating the work site using an illumination device disposed on at least one of the distal ends of the first and second working instruments.

12. The method of claim 1, further including connecting distal ends of the first and second working instruments together after advancing the first and second working instruments to the work site.

13. A method of performing a medical procedure in a patient, the method comprising:
inserting a first working instrument and a second working instrument through an opening in the patient;
creating an incision in body tissue inside the patient using at least one of the first and second working instruments;
advancing the second working instrument through the incision and into a first body cavity to position a distal end of the second working instrument on a first side of tissue at a work site inside the patient;
advancing the first working instrument through a second body cavity and positioning a distal end of the first working instrument on a second side of the tissue such that the first and second working instruments are positioned on opposite sides of the tissue; and
performing a procedure at the work site by manipulating the tissue with the distal end of the first working instrument and the distal end of the second working instrument;
wherein the distal end of the second working instrument advances into the first body cavity without the second working instrument contacting the first working instrument.

14. The method of claim 13, wherein the incision is located in a wall of a third body cavity.

15. The method of claim 13, wherein the first and second working instruments are inserted through a vagina of the patient; the incision is created in a vaginal wall in the patient; and the tissue of the work site includes tissue of a uterine cavity of the patient.

16. The method of claim 1, wherein advancing the first working instrument through the second body cavity comprises abutting a positioning member against a portion of a wall of the second body cavity, the positioning member being disposed on the first working instrument.

17. The method of claim 1, wherein performing procedure includes contacting the second portion of the work site with the first working instrument while treating the first portion of the work site with the second working instrument.

18. The method of claim 13, wherein advancing the first working instrument through the second body cavity comprises abutting a positioning member against a portion of a wall of the second body cavity, the positioning member being disposed on the first working instrument.

19. The method of claim 1, further comprising withdrawing the cutting device from the lumen of the first working instrument or the second working instrument after making the incision, and advancing a second device different from the cutting device through the lumen of the first working instrument or the second working instrument, wherein performing the procedure at the work site includes manipulating tissue with the second device.

20. The method of claim 13, wherein performing the procedure includes removing tissue from the work site.

* * * * *